United States Patent [19]

Boxhoorn et al.

[11] Patent Number: 4,742,034
[45] Date of Patent: May 3, 1988

[54] SILVER ETHYLENE OXIDE CATALYST AND PROCESS FOR PREPARATION OF THE CATALYST

[75] Inventors: Gosse Boxhoorn; Aan H. Klazinga, both of Amsterdam, Netherlands

[73] Assignee: Shell Oil Company, Houston, Tex.

[21] Appl. No.: 41,494

[22] Filed: Apr. 23, 1987

[30] Foreign Application Priority Data

May 7, 1986 [GB] United Kingdom ............... 8611121

[51] Int. Cl.$^4$ .................. B01J 21/04; B01J 23/04; B01J 23/50; B01J 27/12
[52] U.S. Cl. .................................. 502/231; 502/348; 549/534
[58] Field of Search ................ 502/231, 347, 348

[56] References Cited

U.S. PATENT DOCUMENTS 4,123,385 10/1978 Rebsdat et al. ............. 502/348 X
4,248,740 2/1981 Mitsuhata et al. ............. 502/348
4,575,494 3/1986 Young et al. ............. 502/348 X
4,645,754 2/1987 Tamura et al. ............. 502/348 X Primary Examiner—W. J. Shine

[57] ABSTRACT

The invention relates to an improved silver catalyst, suitable for use in the oxidation of ethylene to ethylene oxide, characterized by
(a) a calcined, alkali metal-enriched alumina carrier and
(b) from 1 to 25 percent by weight of metallic silver, based on the weight of the total catalyst,
(c) an alkali metal of the group consisting of potassium, rubidium, cesium and mixtures, in the form of an oxide or hydroxide as a promoter and
(d) a fluoride-anion, the latter two under (c) and (d) each being in an amount between 10 and 1000 parts by weight per million parts by weight of the total catalyst.

16 Claims, No Drawings

SILVER ETHYLENE OXIDE CATALYST AND PROCESS FOR PREPARATION OF THE CATALYST

FIELD OF THE INVENTION

The invention relates to an improved silver catalyst and to a process for preparing such silver catalyst, suitable for use in the oxidation of ethylene to ethylene oxide and to a process for preparing ethylene oxide by the use of such catalyst.

BACKGROUND OF THE INVENTION

It is generally known that silver catalysts are applied in the oxidation of ethylene to ethylene oxide. See for example, U.S. Pat. No. 3,962,136, in which such silver catalysts are disclosed. Moreover there is disclosed in the application that small amounts of one or more promoters are present, such as cesium compounds, rubidium compounds and potassium compounds.

In co-pending U.S. patent application Ser. No. 874,913, filed Jun. 16, 1986, is disclosed a silver catalyst, in which the carrier was enriched with an alkali metal, such as cesium. The catalyst has a high stability in the reaction of ethylene with molecular oxygen to ethylene oxide.

Applicant has now found silver catalysts with improved selectivity and even higher stability.

SUMMARY OF THE INVENTION

The invention relates to an improved silver catalyst, suitable for use in the oxidation of ethylene to ethylene oxide, characterized by a calcined, alkali metal enriched alumina carrier having supported thereon:

(a) from 1 to 25 percent by weight of metallic silver, based on the weight of the total catalyst, (b) an alkali metal of the group consisting of potassium, rubidium, cesium and mixtures thereof, in the form of an oxide or hydroxide as a promoter and (c) a fluoride-anion, the latter two under (b) and (c) each being present in an amount between 10 and 1000 parts by weight per million parts by weight of the total catalyst.

The invention further relates to a process for preparing a silver catalyst, suitable for use in the oxidation of ethylene to ethylene oxide characterized in that an alkali metal enriched alumina carrier, which has been calcined, is impregnated with a solution of a silver compound, sufficient to cause precipitation on the carrier of from 1 to 25 percent by weight, on the total catalyst, of silver, and before, during or after that impregnation also with one or more dissolved potassium-, rubidium- or cesium compounds as promoter and with an additional source of fluoride- anions, and after precipitation the silver compound on the impregnated carrier is reduced to metallic silver.

DESCRIPTION OF THE PREFERRED EMBODIMENTS

The carrier used in the inventive process for the preparation of silver catalysts, is an alkali metal enriched alumina carrier, which has been calcined, preferably to a temperature of between 1200° C. and 1700° C. A large part of the calcined material will be alpha-alumina, but the existence of spinels or other configurations can not be excluded, since the calcined material is enriched with alkali metal. Salts or hydroxide of an alkali metal have been mixed with the original alumina. Suitable salts include fluorides, nitrates, chlorides and sulphates. Suitable metals are lithium, sodium, potassium, rubidium and cesium. Preferred compounds are cesium fluoride, cesium chloride, lithium fluoride, lithium nitrate and cesium hydroxide. Preferably the alkali metal compound is mixed with the alumina in such quantity that the atomic ratio of alkali/aluminum is between 0.0005 and 0.1. If desired silicon dioxide is additionally mixed with the aluminum in such quantity that the atomic ratio of silicon/aluminum is between 0.1 and 0.5. The aluminas may be modifications which by calcination provide alpha-alumina, such like gamma-alumina. Hydrated aluminas may also be suitable, such as boehmite, which latter by calcining via gamma-alumina provides alpha-alumina.

Preferably the alkali metal enriched carrier is prepared by a process comprising mixing an alumina with water and alkali metal salt or hydroxide, extruding the obtained mixture to shaped particles and calcining the shaped particles, preferably to a temperature between 1200° C. and 1700° C. The calcination may be carried out in one or more steps, depending on the choice of alumina modification. Generally a sufficient amount of water is added to form a paste suitable for extrusion. The obtained extrudable paste is then extruded and shaped to particles. The shaped particles are heated in order to evaporate the water. The solid particles are then calcined, preferably to a temperature between 1200° C. and 1700° C. Suitable aluminas are powders of gamma-alumina, alpha-alumina monohydrate, alpha-alumina trihydrate or beta-alumina, monohydrate, which powders during calcination are sintered. At the calcination temperature the crystal structure may be modified. The cubic structure of gamma-alumina is converted into the hexagonal structure of alpha-alumina, depending on the amount and nature of the additive used. The catalytically active surface of the enriched alumina may be between 0.1 and 5 $m^2/g$, preferably between 0.2 and 2 $m^2/g$. The shaped alumina particles comprise, i.a., bars, rings, pellets, tablets and triangles. They are especially suitable in fixed bed applications in ethylene oxide preparation.

In order to prepare a suitable catalyst the calcined, alkali metal enriched alumina carrier is impregnated with a solution of a silver compound sufficient to cause precipitation on the carrier of from 1 to 25 percent by weight, on the total catalyst, of silver, the so impregnated carrier is separated from the solution and the precipitated silver compound is reduced to metallic silver, Hereinafter several detailed methods will be disclosed.

One or more of the alkali metals potassium, nubidium and cesium, preferably in the form of their salts or hydroxides, is added to the silver solution as a promoter. Although the metals potassium, rubidium and cesium in pure metallic from exist, they are in that form not suitable for use. Therefore, they are administered in a solution of their salts or hydroxide. The alumina carrier is impregnated with the promoter before, during or after the impregnation of the silver salt has taken place. The promoter may even be brought of the carrier after reduction to metallic silver has taken place. The amount of promoter generally lies between 10 and 1000 ppm by weight of total catalyst of potassium, rubidium, cesium metal and mixtures thereof. Preferably amounts between 250 and 750 ppm by weight are present on the total catalyst.

The alumina carrier is also impregnated with a source of fluoride-anions. This may be done the same time that the promoter is added, before or later. The function of the F⁻ ions is not quite understood. The amount of fluoride-anions present on the alumina carrier generally is between 10 and 1000 ppm by weight, preferably between 100 and 400 ppm by weight of the total catalyst. Suitable sources of fluoride-anions are ammonium fluoride ($NH_4F$), ammonium hydrogen fluoride ($NH_4HF_2$), lithium flouride, sodium fluoride and silver fluoride.

Generally the alumina carrier is mixed with a silver salt or a silver salt-complex containing aqueous solution, so that the alumina carrier is impregnated with said aqueous solution, thereafter the impregnated carrier is separated from the aqueous solution, e.g. by filtration and then dried. The thus obtained impregnated alumina carrier is heated to a temperature in the range of from 100° C. to 400° C., during a period sufficient to cause reduction of the silver salt (complex) to metallic silver and to form a layer of finely divided silver, which is bound to the surface of the alumina carrier. A reducing gas or an inert gas may be conducted over the alumina carrier during this heating step.

There are know several methods to add the silver to the alumina carrier. The carrier may be impregnated with an aqueous silver nitrate containing solution, and then dried after which drying step the silver nitrate is reduced with hydrogen or hydrozine. The alumina carrier may also be impregnated with an ammoniacal solution of silver oxalate or silver carbonate, and then dried, after which drying step the silver oxalate or silver carbonate is reduced to metallic silver by heating to e.g. up to 400° C. Specific solutions of silver salts with solubilizing and reducing agents may be employed as well, e.g. combinations of vicinal alkanolamines, alkyldiamines and ammonia.

The amount of promoter generally lies between 10 and 1000 ppm of alkali metal calculated on the total carrier material. Preferably amounts between 250 and 750 ppm are especially suitable. Suitable compounds of potassium, rubidium and cesium are, for example, the nitrates, oxalates, carboxylic acid salts or hydroxides. The most preferred promoter is cesium among the alkali metals, preferably applied in an aqueous solution of cesium hydroxide or cesium nitrate.

There are known excellent methods of applying the promoters coincidentally with the silver on the carrier. Suitable alkali metal salts are generally those which are soluble in the silver-precipitating liquid phase. Besides the above-mentioned compounds may be mentioned the nitrates, chlorides, iodides, bromides, bicarbonates, acetates, tartrates, lactates and isopropoxides. The use of alkali metal salts which react with the silver salt in solution must be avoided, e.g. the use of potassium chloride together with silver nitrate in an aqueous solution, since then silver chloride is prematurely precipitated. The use of potassium nitrate is recommended instead of potassium chloride. However, potassium chloride may be used together with a silver salt-amine-complex in aqueous solution, since then silver chloride is not precipitated prematurely from the solution.

The amount of promoter on the alumina carrier may also be regulated within certain limits by washing out the surplus of alkali material with methanol or ethanol. Temperatures, contact times and drying with gases may be regulated. Traces of alcohol in the pores of the carrier must be avoided. High temperature heat treatments can also be utilized to remove or otherwise inactivate a portion of the alkali metal deposited on the surface of the carrier.

A preferred process of impregnating the alumina carrier consists of impregnating the carrier with an aqueous solution containing a silver salt of a carboxylic acid, an organic amine, a salt of potassium, rubidium and/or cesium. A potassium containing silver oxalate solution may be prepared. Silver oxide (slurry in water) is reacted with a mixture of ethylene diamine and oxalic acid, so that an aqueous solution of silver oxalate-ethylene diamine-complex is obtained, to which solution is added a certain amount of potassium compound. Other amines, such as ethanolamine, may be added as well. A potassium containing silver oxalate solution may also be prepared by precipitating silver oxalate from a solution of potassium oxalate and silver nitrate and rinsing with water or alcohol the obtained silver oxalate in order to remove the adhering potassium salt until the desired potassium content is obtained. The potassium containing silver oxalate is then solubilized with ammonia and/or an amine in water. Rubidium and cesium containing solutions may be prepared also in these ways. The impregnated alumina carriers are then heated to a temperature between 100° C. and 400° C., preferably between 125° C. and 325° C.

It is observed that independent of the form in which the silver is present in the solution before precipitation on the carrier, the term "reduction to metallic silver" is used, while in the meantime often decomposition by heating occurs. We prefer to use the term "reduction", since the positively charged $Ag^+$ ion is converted into metallic Ag atom. Reduction times may generally vary from 5 min to 8 hours, depending on the circumstances.

The promoter on the alumina surface is preferably present in the form of an oxide of potassium, rubidium or cesium. Mixtures of oxides are not excluded.

The instant invention thus comprises a silver catalyst, suitable for use in the oxidation of ethylene to ethylene oxide which comprises:

(a) an alkali metal-enriched carrier prepared by a process which comprises:

(i) mixing an anhydrous or hydrated alumina with water and cesium fluoride or chloride wherein the atom ratio of cesium/aluminum is between about 0.0005 and about 0.1, (ii) shaping and calcining the mixture of (i) at a temperature ranging from about 1200° C. to about 1700° C. to obtain an alkali metal enriched alumina carrier, (b) from about 1 to about 25 percent by weight of metallic silver, based on the weight of the total catalyst, deposited on the surface of the carrier, (c) from about 10 to about 1000 ppm by weight of the total catalyst of a cesium promoter, deposited on the surface of the carrier, and (d) from about 100 to about 400 ppm by weight of the total catalyst of a fluoride-anion, deposited on the surface of the carrier.

The instant invention further comprises a process for the preparation of a silver-containing catalyst suitable for the oxidation of ethylene to ethylene oxide which comprises:

(a) mixing an anhydrous or hydrated alumina with water, cesium fluoride or chloride wherein the atom ratio of cesium/aluminum (oxide) is between about 0.0005 and about 0.1, (b) shaping and calcining the mixtures of (a) at a temperature ranging from about 1200° C. to about 17000° C. to obtain an alkali metal enriched alumina carrier, and (c) applying to the carrier a silver compound, a cesium promoter and a fluoride-anion sufficient to apply from about 1 to about 25 percent of the total catalyst of silver, from about 20 to about 1000 ppm of cesium promoter by weight of the total catalyst and from about 100 to about 400 ppm by weight of the total catalyst of a fluoride-anion and converting said silver compound to metallic silver.

The silver catalysts according to the present invention have been shown to be particularly selective and stable catalysts in the direct oxidation of ethylene with molecular oxygen to ethylene oxide. The conditions for carrying out such an oxidation reaction in the presence of the silver catalysts according to the present invention broadly comprise those already described in the prior art. This applies, for example, to suitable temperatures, pressures, residence times, diluent materials, such as nitrogen, carbon dioxide, steam, argon, methane or other saturated hydocarbons, presence or absence of moderating agents to control the catalytic action, for example, 1-2-dichloroethane, vinyl chloride or chlorinated polyphenyl compounds, the desirability of employing recycle operations or applying successive conversion in different reactors to increase the yields of ethylene oxide, and any other special conditions which may be selected in processes for preparing ethylene oxide. Pressures in the range of from atmospheric to 35 bar are generally employed. Higher pressures are, however, by no means excluded. Molecular oxygen employed as reactant can be obtained from conventional sources. The suitable oxygen charge may consist essentially of relatively pure oxygen, a concentrated oxygen stream comprising oxygen in major amount with lesser amounts of one or more diluents, such as nitrogen and argon, or another oxygen-containing stream, such as air. It is therefore evident that the use of the present silver catalysts in ethylene oxidation reactions is in no way limited to the use of specific conditions among those which are known to be effective.

In a preferred application of the silver catalysts according to the present invention, ethylene oxide is produced when an oxygen-containing gas is contacted with ethylene in the presence of the present catalysts at a temperature in the range of from 190° C. to 285° C. and preferably 200° C. to 270° C.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

Generally in the reaction of ethylene with oxygen to ethylene oxide, the ethylene present is at least a double amount (on a mol basis) compared with the oxygen, but the applied amount of ethylene is often much higher. Therefore the conversion is calculated according to the mol percentage of oxygen, which has been used. The oxygen conversion is dependent on the reaction temperature, which latter is a measure for the activity of the catalyst employed. The values $T_{30}$, $T_{40}$ and $T_{50}$ indicate the temperatures at 30 mol %, 40 mol % and 50 mol % conversion of the oxygen respectively in the reactor, and the values T are expressed in °C. These temperatures are higher when the conversion of the oxygen is higher. Moreover these temperatures are strongly dependent on the employed catalyst and reaction conditions. The selectivities (to ethylene oxide) indicate the molar percentage of ethylene oxide in the reaction mixture compared with the total molar amount of converted matter. The selectivity is indicted e.g. as $S_{30}$, $S_{40}$ and $S_{50}$, which means the selectivity at 30, 40 and 50 mol % oxygen conversion respectively.

The stability of the silver catalyst cannot be expressed directly. To measure the stability, experiments during a considerable time, e.g. a year would be necessary. Applicant has now found that these time consuming tests can be simulated by carrying out the experiments during about one month under the extreme high velocity of thirty thousand liters gas (liter catalyst)$^{-1}$h$^{-1}$, also indicated as GHSV). This velocity is much higher than that used in commercial ethylene oxide processes (the latter GHSV=2800–8000). During the whole test period the above defined S and T values are measured regularly. After the reaction has finished, the total amount of produced ethylene oxide per ml of catalyst is determined. The selectivity and the activity of the catalyst are extrapolated on the basis that one ml of catalyst would have produced 1000 g of ethylene oxide. The new catalyst is considered to be more stable than a standard catalyst, if the differences in T- and S-values, measured on the new catalyst (preferably at the beginning and at the end of the reaction) are smaller than those measured on the standard catalyst, which in every experiment is present. The stability tests are carried out at constant oxygen conversion of 35%.

EXAMPLE 1

A. 8 g of cesium fluoride dissolved in 832 ml water was mixed with 800 g of Kaiser alumina (26405) (Al$_2$O$_3$.H$_2$O) by addition of the cesium fluoride solution of the alumina, and the mixture was kneaded during 30 min. The obtained paste was extruded. The obtained shaped pieces were dried at 120° C. and then calcined at periodically increased temperature. Up to 700° C. was calcined firstly at an increase in temperature of 200° C./h, then was calcined for one hour at 700° C., whereafter the temperature in two hours reached 1600° C. Finally was calcined further for one hour at 1600° C. The pore volume of the alpha-alumina shaped pieces was 0.45 ml/g and the average pore diameter was 1.6 μm. The obtained ring-shaped pieces were impregnated with an aqueous solution of silver oxalate, to which cesium hydroxide and ammonium fluoride was added. The impregnation was carried out for 10 min under vacuum, whereafter the shaped pieces were separated from the aqueous solution, and then placed in a heat air stream at a temperature of 250°–270° C. during 10 min, in order to convert the silver oxalate into metallic silver. The aqueous solution of silver oxalate contained 28 percent by weight of Ag (calculated on the total weight of the solution), wherein the silver oxalate was complexed with ethylene diamine and to which solution was added cesium hydroxide and ammonium fluoride. The impregnated shaped pieces before heat treatment contained 17.1 percent by weight (calculated one the weight of the total catalyst) of silver and 280 ppm of cesium and 200 ppm of F (calculated on one million parts by weight of total catalyst).

B. A second catalyst was prepared in the same manner as above described, except that the amount of cesium as promoter was 330 ppm.

Both silver catalysts were employed in the preparation of ethylene oxide from ethylene and oxygen. A cylindric steel reactor with a length of 40 cm and a diameter of 5 mm was completely filled with crushed catalyst particles of about 1 mm. The reactor was placed in a bath of silica and alumina particles in fluid bed state. A gas mixture of the following composition was introduced into the reactor: 30 mol % ethylene, 8.5 mol % oxygen, 7 mol % carbon dioxide and 54.5 mol % nitrogen and 5.5 ppm vinyl chloride as moderator. The GHSV was 3300h$^{-1}$. The pressure was maintained at 15 bar and the temperature dependent on the oxygen conversion. Measuring-instruments were connected to the reactor and to a computer, such that conversion and reaction temperature could be precisely regulated. With the aid of gaschromatography and mass-spectroscopy the amounts of reaction products were determined. The oxygen conversion was 40%.

A third catalyst was prepared according to Example 1A, with the exception that ammonium fluoride was not added.

All three catalysts were tested on their selectivity: The selectivity values ($S_{40}$) of the first and the second catalyst were 81.2 and 81.3, while the selectivity ($S_{40}$) of the third catalyst was 79.9.

All three catalysts did not differ substantially in activity. It proved that the addition of fluoride anions considerably improved the selectivity of the catalyst.

EXAMPLE 2

5.34 g of cesium fluoride was dissolved in 1070 ml water. 800 g of Kaiser alumina (26405) (Al$_2$O$_3$.H$_2$O) and 166.8 g of silicon dioxide (150 g of dry compound) were mixed and the mixture was kneaded for 15 min. In one minute the CsF solution was added to the mixture and the mixture was again kneaded. The obtained paste was then extruded. The obtained shaped pieces were dried for one hour at 120° C. and then calcined at periodically increased temperature. Up to 500° C. was firstly calcined at an increase in temperature of 200° C./h, then was calcined for one hour at 500° C., whereafter the temperature in two hours reached 1600° C. Finally was calcined for six hours at 1600° C. The pore volume of the shaped pieces was 0.25 ml.g$^{-1}$ and the average pore diameter 1.3 μm.

The ring-shaped pieces were impregnated with an aqueous solution of silver oxalate, to which solution cesium hydroxide and ammonium fluoride was added. The impregnation was carried but for 10 min in vacuum, whereafter the shaped pieces were separated from the solution and then placed in a stream of heated air for 10 min at a temperature of 250°–270° C., in order to convert the silver oxalate in metallic silver. The aqueous solution of silver oxalate was a 28 percent by weight containing silver solution, wherein the silver oxalate was complexed with ethylene diamine and to which solution the necessary additives were added. The impregnated shaped pieces before heat treatment containing 13.4 percent by weight of silver (calculated on the total weight of the catalyst), 660 ppm of cesium and 200 ppm of fluorine (calculated on one million prts by weight of total catalyst).

The silver catalyst was employed in the preparation of ethylene oxide from ethylene and oxygen. A cylindric steel reactor with a length of 40 cm and a diameter of 5 mm was completely filled with crushed catalyst particles of about 1 mm. The reactor was then placed in a bath of silica and alumina particles maintained in fluid bed. A gas mixture of the following composition was introduced into the reactor: 30 mol % ethylene, 8.5 mol % oxygen, 7 mol % carbon dioxide and 54.5 mol % nitrogen and 5.5 ppm vinylchloride as moderator. The GHSV was 3300 h$^{-1}$. The pressure was maintained at 15 bar and the temperature was dependent on the oxygen conversion, the latter being 40%. Measuring-instruments were connected to the reactor and to a computer, such that conversion and reaction temperature could be precisely regulated. With the aid of gaschromatography and mass-spectroscopy the amounts of reaction products could be determined.

The selectivity ($S_{40}$) of the above-mentioned silver catalyst was 81.5, while the selectivity ($S_{40}$) of a non-ammonium fluoride doped silver catalyst was 80.1.

EXAMPLE 3

1.79 g of cesium fluoride dissolved in 861 ml water was mixed with 810 g of Kaiser alumina (26405) (Al$_2$O$_3$.H$_2$O) by addition of the cesium fluoride solution to the alumina, and the mixture was kneaded during 30 min. The obtained paste was extruded. The obtained shaped pieces were dried at 120° C. and then calcined at periodically increased temperature. Up to 500° C. was calcined firstly at an increase in temperature of 200° C./h, then was calcined for one hour at 500° C., whereafter the temperature in two hours reached 1600° C. Finally was calcined further for six hours at 1600° C. The pore volume of the alpha-alumina shaped pieces was 0.50 ml/g and the average pore diameter was 1.2 μm.

The obtained ring-shaped pieces were impregnated with an aqueous solution of silver oxalate, to which cesium hydroxide and ammonium fluoride was added. The impregnation was carried out for 10 min under vacuum, whereafter the shaped pieces were separated from the aqueous solution, and then placed in a heated air stream at a temperature of 250°–270° C. during 10 min, in order to convert the silver oxalate into metallic silver. The aqueous solution of silver oxalate contained 28 percent by weight of Ag (calculated on the total weight of the solution), wherein the silver oxalate was complexed with ethylene diamine and to which solution was added cesium hydroxide and ammonium fluoride. The impregnated shaped pieces before heat treatment contained 16.9 percent by weight (calculated on the weight of the total catalyst) of silver and 600 ppm of cesium and 200 ppm of F (calculated on one million parts by weight of total catalyst).

The silver catalyst was employed in the preparation of ethylene oxide from ethylene and oxygen. A cylindric steel reactor with a length of 40 cm and a diameter of 5 mm was completely filled with crushed catalyst particles of about 1 mm. The reactor was placed in a bath of silica and alumina particles in fluid bed state. A gas mixture of the following composition was introduced into the reactor: 30 mol % ethylene, 8.5 mol % oxygen, 7 mol % carbon dioxide and 54.5 mol % nitrogen and 5.5 ppm vinyl chloride as moderator. The GHSV was 3300 h$^{-1}$. The pressure was maintained at 15 bar and the temperature dependent on the oxygen conversion. Measuring-instruments were connected to the reactor and to a computer, such that conversion and reaction temperature could be precisely regulated. With the aid of gaschromatography and mass-spectroscopy the amounts of reaction products were determined. The oxygen conversion was 40%. The selectivity ($S_{40}$) of the above-mentioned silver catalyst was 82.5.

EXAMPLE 4

The silver catalyst prepared according to the process disclosed in Example 1A and the silver catalyst prepared by the process disclosed in Example 3 were both tested on their stability in the reaction of ethylene to ethylene oxide.

A steel cylindric reactor with a length of 15 cm and a diameter of 3 mm was filled completely with catalyst particles of about 0.3 mm. The reactor was placed in a bath, which consisted of silicon/aluminum particles in a fluidized state. A gas mixture with the following composition was conducted through the reactor: 30 mol % ethylene, 8.5 mol % oxygen, 7 mol % carbon dioxide and 54.5 mol % nitrogen and 7 parts, per million parts of gas, of vinylchloride as moderator. The GHSV was 30,000 $ll^{-1}h^{-1}$. The pressure was 15 bar and the temperature was dependent of the oxygen conversion. The measuring instruments were connected to the reactor and to a computer, in such a way that conversion and temperature could be regulated precisely. With the aid of gas chromatography or mass spectroscopy the content of each reaction component was determined. The stability test was carried out at a constant oxygen conversion of 35% During the test, at regular intervals, the reaction temperature at 35% oxygen conversion was determined. Also the selectivity to ethylene oxide was determined at regular intervals. After 40 days the tests were discontinued and the total amount of produced ethylene oxide per ml catalyst was determined.

From the measured reaction temperatures, starting at the beginning of the reaction, the increase in reaction temperature was calculated in °C. for the moment at which 1000 g ethylene oxide per ml catalyst would have been produced ($\Delta T^{1000}$). From the measured selectivities, starting at the beginning of the reaction the decrease in selectivity in mol % was calculated for the moment at which 1000 g ethylene oxide per ml catalyst would have been produced ($\Delta S^{1000}$).

The same measurements and calculations were carried out with a third silver catalyst which did not contain fluorine, but which still contained cesium fluoride in its carrier and which further in all aspects was prepared in the same way as the inventive catalysts.

In the Table the $\Delta S^{1000}$ and $\Delta T^{1000}$ are given in the percentage of the $\Delta S^{1000}$ and $\Delta T^{1000}$ at the third catalyst, that is, $\Delta S^{1000}$ for Example 1 is divided by $\Delta S^{1000}$ for the third catalyst times 100% to provide the percentage value for $\Delta S^{1000}$ for Example 1, etc.

| CATALYST | | | |
| --- | --- | --- | --- |
| CARRIER enriched with | NH$_4$F applied | $\Delta S^{1000}$ % | $\Delta T^{1000}$ % |
| CsF | YES (ex.1A) | 81 | 100 |
| CsF | YES (es.3) | 43 | 91 |
| CsF | NO | 100 | 100 |

We claim:

1. A silver catalyst, suitable for use in the oxidation of ethylene to ethylene oxide comprising a calcined, alkali metal-enriched alumina carrier having supported thereon:
   (a) from 1 to 25 percent by weight of metallic silver, based on the weight of the total catalyst,
   (b) an alkali metal of the group consisting of potassium, rubidium, cesium and mixtures thereof in the form of an oxide or hydroxide as a promoter and
   (c) a fluoride-anion, the latter two under (b) and (c) each being present in an amount between 10 and 1000 ppm by weight of the total catalyst.

2. The silver catalyst according to claim 1 wherein the amount of alkali metal as defined under (b) is between 250 and 750 ppm by weight of the total catalyst.

3. The silver catalyst according to claim 1 wherein the amount of fluoride-anion is between 100 and 400 ppm by weight of total catalyst.

4. The silver catalyst according to claim 1 wherein the amount of alkali metal as defined under (b) is between 250 and 750 ppm by weight and the amount of fluoride-anion is between 100 and 400 ppm by weight.

5. The silver catalyst according to any one of the claims 1-3 wherein the alkali metal-enriched alumina carrier contains cesium as the alkali metal.

6. A silver catalyst, suitable for use in the oxidation of ethylene to ethylene oxide comprising:
   (a) an alkali metal-enriched carrier prepared by a process which comprises:
      (i) mixing an anhydrous or hydrated alumina with water and cesium fluoride or chloride wherein the atom ratio of cesium/aluminum is between about 0.0005 and about 0.1,
      (ii) shaping and calcining the mixtures of (i) at a temperature ranging from about 1200° C. to about 1700° C. to obtain an alkali metal enriched alumina carrier,
   (b) from about 1 to about 25 percent by weight of metallic silver, based on the weight of the total catalyst, deposited on the surface of the carrier,
   (c) from about 10 to about 1000 ppm by weight of the total catalyst of a cesium promoter, deposited on the surface of the carrier, and
   (d) from about 100 to about 400 ppm by weight of the total catalyst of a fluoride-anion, deposited on the surface of the carrier.

7. A process for preparing the silver catalyst of claim 1 which process comprises impregnating an alkali metal enriched alumina carrier which has been prepared by mixing an alumina with water and a salt of an alkali metal and calcining at a temperature between 1200° C. and 1700° C. with a solution of a silver compound, sufficient to cause precipitation on the carrier of from 1 to 25 percent by weight, on the total catalyst, of silver, and before, during or after said silver impregnation, impregnating the carrier with one or more dissolved potassium, rubidium or cesium compounds as promoter and with an additional source of fluoride anions and after precipitation, the silver compound on the impregnated carrier is reduced to metallic silver.

8. The process according to claim 7 wherein the alumina carrier is mixed with cesium fluoride, cesium chloride, lithium fluoride, lithium nitrite or cesium hydroxide.

9. The process according to claim 7 wherein an alkali metal compound is mixed with the alumina in such quantity that the atomic ratio of alkali/aluminum is between 0.0005 and 0.1.

10. The process according to claim 9 wherein silicon dioxide is additionally mixed with the alumina in such quantity that the atomic ratio of silicon/aluminum is between 0.1 and 0.5.

11. The process according to claim 7 wherein the promoter is present in an amount between 250 and 750 ppm by weight.

12. The process according to any one of the claims 7-10 and 11 wherein the source of fluoride-anions is ammonium fluoride or ammonium hydrogen fluoride.

13. The process according to any one of the claims 7-10 and 11 wherein the source of fluoride-anions is lithium fluoride, sodium fluoride or silver fluoride.

14. The process according to claim 7 wherein the amount of fluoride-anions is between 100 and 400 ppm by weight of total catalyst.

15. A process for the preparation of a silver-containing catalyst suitable for the oxidation of ethylene to ethylene oxide which comprises:
 (a) mixing an anhydrous or hydrated alumina with water, cesium fluoride or chloride wherein the atom ratio of cesium/aluminum (oxide) is between about 0.0005 and about 0.1,
 (b) shaping and calcining the mixture of (a) at a temperature ranging from about 1200° C. to about 1700° C. to obtain an alkali metal enriched alumina carrier, and
 (c) applying to the carrier a silver compound, a cesium promoter and a fluoride-anion sufficient to apply from about 1 to about 25 percent by weight of the total catalyst of silver, from 20 to about 1000 ppm of cesium promoter by weight of the total catalyst and from about 100 to about 400 ppm by weight of the total catalyst of a fluoride-anion and converting said silver compound to metallic silver.

16. A silver catalyst, suitable for use in the oxidation of ethylene to ethylene oxide prepared by the process according to any one of the claims 7-10, 11-14 and 15.

* * * * *